US012009066B2

(12) United States Patent
Morones et al.

(10) Patent No.: US 12,009,066 B2
(45) Date of Patent: Jun. 11, 2024

(54) AUTOMATED TRANSITIVE READ-BEHIND ANALYSIS IN BIG DATA TOXICOLOGY

(71) Applicant: International Business Machines Corporation, Armonk, NY (US)

(72) Inventors: Rebecca Morones, Berthoud, CO (US); Sarah K. Czaplewski-Campbell, Rochester, MN (US); Melissa K. Miller, Research Triangle Park, NC (US); Mary E. Rudden, Denver, CO (US); Craig M. Trim, Ventura, CA (US)

(73) Assignee: International Business Machines Corporation, Armonk, NY (US)

(*) Notice: Subject to any disclaimer, the term of this patent is extended or adjusted under 35 U.S.C. 154(b) by 808 days.

(21) Appl. No.: 16/419,100

(22) Filed: May 22, 2019

(65) Prior Publication Data

US 2020/0372977 A1 Nov. 26, 2020

(51) Int. Cl.
*G16C 20/30* (2019.01)
*G06F 9/54* (2006.01)
(Continued)

(52) U.S. Cl.
CPC .............. *G16C 20/30* (2019.02); *G06F 9/542* (2013.01); *G06F 17/18* (2013.01); *G06N 5/02* (2013.01); *G16C 20/10* (2019.02); *G16C 20/70* (2019.02)

(58) Field of Classification Search
CPC ........ G16C 20/30; G16C 20/10; G16C 20/70; G16C 20/40; G06F 9/542; G06F 17/18; G06N 5/02; G06N 5/022
See application file for complete search history.

(56) References Cited

U.S. PATENT DOCUMENTS 6,421,612 B1 * 7/2002 Agrafiotis ............ G06K 9/6251
702/19
8,597,875 B2 12/2013 van Ravenzwaay et al.
(Continued)

FOREIGN PATENT DOCUMENTS

CN 104615901 A 5/2015
CN 104995625 A 10/2015
(Continued)

OTHER PUBLICATIONS

WO-2023009513-A1_translated (Year: 2023).*
(Continued)

*Primary Examiner* — Manish S Shah
*Assistant Examiner* — Michael J Singletary
(74) *Attorney, Agent, or Firm* — Patterson + Sheridan, LLP

(57) ABSTRACT

Techniques for probabilistic analysis of chemicals are provided. An indication of a proposed chemical composition is received. A predicted toxicity score is generated for the proposed chemical composition by performing probabilistic analysis on the proposed chemical composition. The probabilistic analysis includes identifying, based on a knowledge graph, at least one similar composition that is structurally similar to the proposed chemical composition. The analysis also includes identifying a set of chemical reactions that include the at least one similar composition, and determining one or more products of the identified set of chemical reactions. The probabilistic analysis further includes determining a toxicity of at least one of the one or more products. Finally, the predicted toxicity score is returned.

20 Claims, 6 Drawing Sheets

(51) Int. Cl.
*G06F 17/18* (2006.01)
*G06N 5/02* (2023.01)
*G16C 20/10* (2019.01)
*G16C 20/70* (2019.01)

(56) References Cited

U.S. PATENT DOCUMENTS

| | | | |
|---|---|---|---|
| 9,424,517 B2 | 8/2016 | Daulton et al. | |
| 9,783,852 B2 | 10/2017 | Suzuki et al. | |
| 9,790,545 B2 | 10/2017 | Pennings et al. | |
| 2007/0219768 A1* | 9/2007 | Ekins | G16C 20/30 703/11 |
| 2014/0278130 A1* | 9/2014 | Bowles | G16B 25/10 702/19 |
| 2015/0371009 A1* | 12/2015 | Chen | G16C 20/50 702/19 |
| 2017/0270239 A1 | 9/2017 | Grafstrom et al. | |
| 2018/0285731 A1* | 10/2018 | Heifets | G16C 20/70 |
| 2020/0043567 A1* | 2/2020 | Siva Kumar | G06N 20/00 |
| 2023/0086047 A1* | 3/2023 | Porada | G16H 70/40 424/9.2 |

FOREIGN PATENT DOCUMENTS

| | | | | |
|---|---|---|---|---|
| CN | 108268749 A | * | 7/2018 | G06K 9/00 |
| CN | 108920889 A | * | 11/2018 | |
| CN | 108920889 A | | 11/2018 | |
| KR | 101721188 B1 | * | 3/2017 | |
| KR | 101721188 B1 | | 3/2017 | |
| WO | 200235495 A1 | | 5/2002 | |
| WO | 200537419 A2 | | 4/2005 | |
| WO | WO-2012042541 A2 | * | 4/2012 | C07D 459/00 |
| WO | WO-2023009513 A1 | * | 2/2023 | G01N 15/1429 |

OTHER PUBLICATIONS

PCT Notification of Transmittal of the International Search Report and the Written Opinion of the International Searching Authority, or the Declaration for Application No. PCT/IB2020/054678 dated Aug. 31, 2020.

Alexious Koutsoukas et al., "Predictive Toxicology: Modeling Chemical Induced Toxicological Response Combining Circular Fingerprints with Random Forest and Combing Circular Fingerprints with Random Forest and Support Vector Machine Enviromental Information and Remote Sensing," Mar. 2, 2016 pp. 2-7.

Emilio Benfenati "Predicting toxicity through computers: a changing world" Chemistry Central Journal Dec. 18, 2007, pp. 1-7.

Schmidt, U., Struck, S., Gruening, B. et al. (2008). SuperToxic: a comprehensive database of toxic compounds. Nucleic acids research, 37(suppl_1), D295-D299.

"Chemsec: Sin List," Chemsec: International Chemical Secretariat, Date Accessed: Oct. 25, 2022, pp. 1-2 http://chemsec.org/business-tool/sin-list/.

"ChemSec: SINimilarity," ChemSec: Sin List, Date Accessed: Oct. 25, 2022, pp. 1-3 http://chemsec.org/what-we-do/sinimilarity.

* cited by examiner

AUTOMATED TRANSITIVE READ-BEHIND ANALYSIS IN BIG DATA TOXICOLOGY

BACKGROUND

The present disclosure relates to knowledge graphs, and more specifically, to constructing and using knowledge graphs to predict chemical effects.

Many chemical substances, such as volatile organic compounds (VOCs), can have deleterious effects on health and the environment. For this reason, chemicals are often manually analyzed and reviewed by subject matter experts in order to understand the potential risks and effects of a given substance. For example, when a new product is developed, significant efforts are required to ensure that the product will not include, release, or otherwise emit substances that are potentially dangerous or toxic. In some instances, experts have resorted to manual testing (e.g., in human trials or using animal testing) to identify harmful substances. However, this testing is time-consuming, expensive, and involves potential moral hazards. Additionally, traditional toxicology analysis using established literature or chemical analysis is subjective, error-prone, and requires significant knowledge of the domain.

SUMMARY

According to one embodiment of the present disclosure, a method is provided. The method includes receiving an indication of a proposed chemical composition. The method further includes generating a predicted toxicity score for the proposed chemical composition by performing, by operation of one or more computer processors, a probabilistic analysis on the proposed chemical composition. Performing the probabilistic analysis includes identifying, based on a knowledge graph, at least one similar composition that is structurally similar to the proposed chemical composition. The probabilistic analysis further includes identifying a set of chemical reactions that include the at least one similar composition, and determining one or more products of the identified set of chemical reactions. Additionally, the probabilistic analysis includes determining a toxicity of at least one of the one or more products. Finally, the method includes returning the predicted toxicity score.

According to a second embodiment of the present disclosure, a computer-readable storage medium is provided. The computer-readable storage medium has computer-readable program code embodied therewith, the computer-readable program code executable by one or more computer processors to perform an operation. The operation includes receiving an indication of a proposed chemical composition. The operation further includes generating a predicted toxicity score for the proposed chemical composition by performing a probabilistic analysis on the proposed chemical composition. Performing the probabilistic analysis includes identifying, based on a knowledge graph, at least one similar composition that is structurally similar to the proposed chemical composition. The probabilistic analysis further includes identifying a set of chemical reactions that include the at least one similar composition, and determining one or more products of the identified set of chemical reactions. Additionally, the probabilistic analysis includes determining a toxicity of at least one of the one or more products. Finally, the operation includes returning the predicted toxicity score.

According to a third embodiment of the present disclosure, a system is provided. The system includes one or more computer processors, and a memory containing a program which, when executed by the one or more computer processors, performs an operation. The operation includes receiving an indication of a proposed chemical composition. The operation further includes generating a predicted toxicity score for the proposed chemical composition by performing a probabilistic analysis on the proposed chemical composition. Performing the probabilistic analysis includes identifying, based on a knowledge graph, at least one similar composition that is structurally similar to the proposed chemical composition. The probabilistic analysis further includes identifying a set of chemical reactions that include the at least one similar composition, and determining one or more products of the identified set of chemical reactions. Additionally, the probabilistic analysis includes determining a toxicity of at least one of the one or more products. Finally, the operation includes returning the predicted toxicity score.

DETAILED DESCRIPTION

Embodiments of the present disclosure provide techniques for automated transitive and read-behind analysis on proposed substances and products in order to generate objective predictions regarding toxicity, environmental effects, and the like. These predicted effects can help determine whether the substance should be pursued or modified. Additionally, in some embodiments, the systems disclosed herein can further generate gap measures indicating a level of inherent risk in pursuing the substance, in terms of how much is known about the structure the existing literature. For example, a substance that is chemically similar to known substances may be more safely developed, as compared to a substance that is dissimilar from all known literature. That is, if the proposed substance is not similar to any known literature, the new substance carries more inherent risk and uncertainty because there is no way to reliably predict what the effects may be.

In some embodiments, a system uses a probabilistic reasoner to perform accurate read-across analysis on chemical compositions. In embodiments, this analysis includes not only identification of similar substances and chemicals, but also examination of the cumulative and synergistic effects that can occur when chemicals interact and react. In this way, embodiments of the present disclosure provide a more detailed and more accurate determination as to the potential effects of a given chemical composition. In one embodiment, determining predicted effects for chemical substances includes determining toxicity for humans or other animals, environmental effects, and the like. In some embodiments, the systems disclosed herein can further determine the likelihood that newly proposed substances will eventually be banned or otherwise regulated, as discussed in more detail below. Additionally, in one embodiment, the system determines a gap measure between the substance and known compositions, in order to determine how uncertain the effects are.

Figure 1:
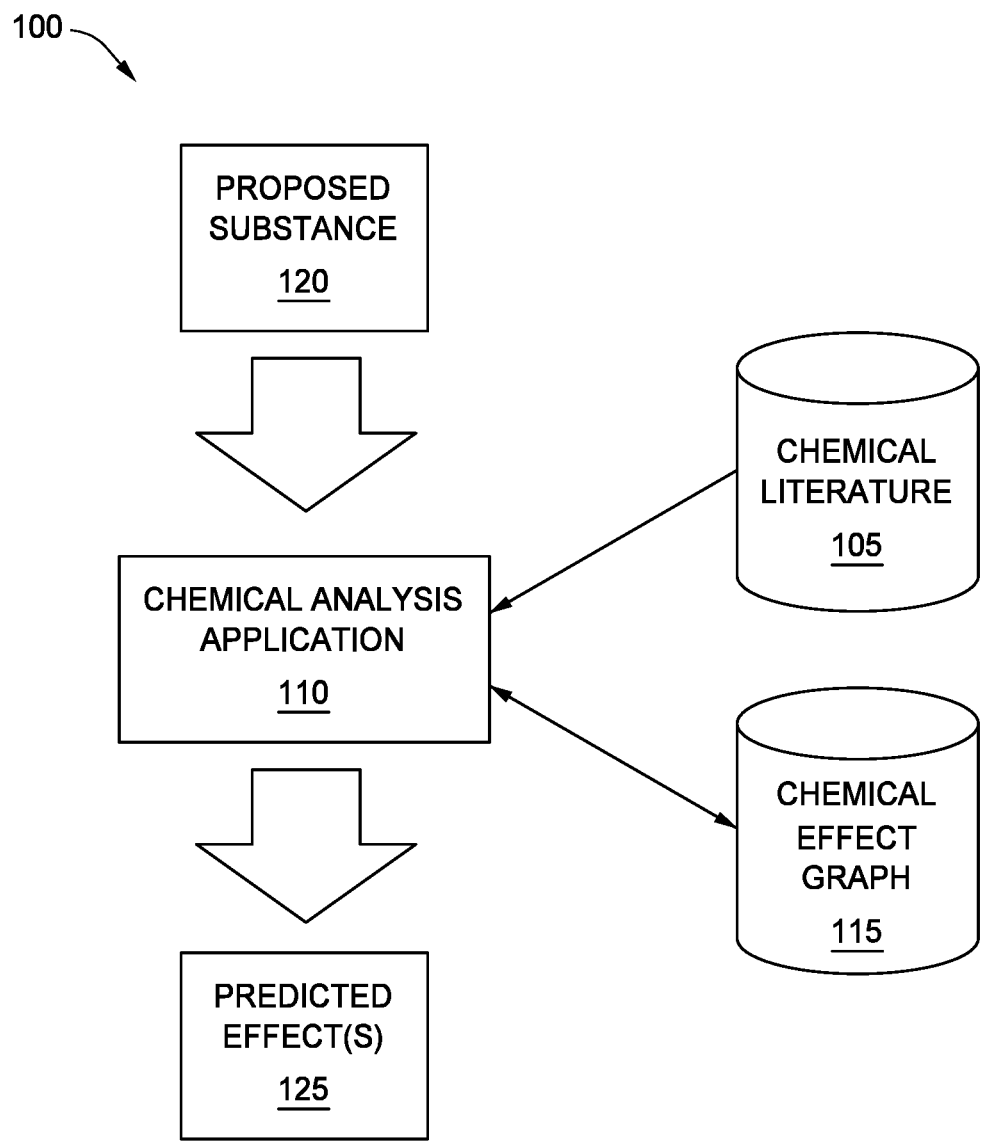
FIG. 1 illustrates a workflow for automatically ingesting chemical literature to generate knowledge graphs and analyze newly proposed substances, according to one embodiment disclosed herein.

FIG. 1 illustrates a workflow 100 for automatically ingesting chemical literature to generate knowledge graphs and analyze newly proposed substances, according to one embodiment disclosed herein. In the illustrated embodiment, a Chemical Analysis Application 110 receives or retrieves Chemical Literature 105 in order to generate one or more Chemical Effect Graph(s) 115. In embodiments, the Chemical Literature 105 may reside on any number of devices or locations. In an embodiment, the Chemical Literature 105 corresponds to existing documentation, research, publications, studies, and the like that have been completed to study the effects of chemicals, elements, compositions, compounds, and/or substances. For example, in an embodiment, the Chemical Literature 105 can include studies regarding accidental exposure to a substance, experimental exposure, comparisons between effects, and the like. In one embodiment, the Chemical Literature 105 also includes documentation regarding reactions between chemicals. Additionally, in some embodiments, the Chemical Literature 105 includes regulatory information, such as restrictions or bans related to chemicals or chemical compositions.

In the illustrated embodiment, the Chemical Analysis Application 110 parses the documents included in the Chemical Literature 105, such as using natural language processing (NLP), to generate a Chemical Effect Graph 115. In one embodiment, the Chemical Effect Graph 115 is a knowledge graph, where each node in the graph is a chemical or chemical composition, and where edges or connections in the graph indicate learned similarity between the chemical(s) represented by each node, and/or reactivity between the corresponding chemical(s). In an embodiment, the Chemical Analysis Application 110 ingests the Chemical Literature 105 to identify chemicals and, for each chemical, determine the structure and characteristics, identify any known effects or regulations related to the chemical, determine any known reactions between the chemical and other chemical(s), and the like. This information is then represented in the Chemical Effect Graph 115. In one embodiment, using this Chemical Effect Graph 115, the Chemical Analysis Application 110 can utilize probabilistic reasoning along transitive pathways in the graph, to identify potential toxic and environmental effects of new compounds before they are tested, by comparing the chemical structure to known and tested compounds and reactions.

As illustrated, the Chemical Analysis Application 110 can thereafter receive an indication of a Proposed Substance 120 (e.g., from a user), and perform probabilistic analysis on the Proposed Substance 120 to generate a set of Predicted Effect(s) 125, using the Chemical Effect Graph 115. In one embodiment, the Proposed Substance 120 includes a list of chemical(s) and/or composition(s) that the user intends to develop, include as part of a product, or otherwise use. For example, the Proposed Substance 120 may correspond to an herbicide currently in development, a new medication being researched, a substance that is used to make or prepare a product, and the like. In an embodiment, the Predicted Effect(s) 125 can include toxicological effects (e.g., predicted toxicity or otherwise harmful effects that humans and/or animals may suffer after exposure to the Proposed Substance 120), environmental effects (e.g., whether it is benign, short-lived in the environment, bio-accumulative, and the like), and the like. In some embodiments, the Predicted Effects 125 include an indication as to the predicted exposure required to experience the effects (e.g., in terms of the amount of the chemical, the time of exposure, and the like).

In some embodiments, the Predicted Effects 125 can also include a likelihood that the Proposed Substance 120 will be banned or otherwise regulated. For example, the Chemical Analysis Application 110 can determine similarities between the Proposed Substance 120 and other substances which are currently subject to regulations by the relevant entities (e.g., national or local governments). Based on these similarities, the Chemical Analysis Application 110 can determine how likely it is that the Proposed Substance 120 will be similarly regulated. Additionally, in some embodiments, the Chemical Analysis Application 110 generates a gap measure indicating a level of certainty (or uncertainty) surrounding the Proposed Substance 120. For example, if only twenty percent of the structure of the Proposed Substance 120 is able to be analyzed against existing literature, the Chemical Analysis Application 110 can indicate that there is significant uncertainty and risk for the Proposed Substance 120.

In one embodiment, the user can specify which effects and measures they wish to review. In an embodiment, based on these Predicted Effects 125, the user can determine the probability that the Proposed Substance 120 will be abandoned (e.g., due to risk, regulation, toxicity, and the like) before significant time or efforts are expended developing and researching it. Additionally, using the Chemical Analysis Application 110, the user can suggest modifications or alternatives to the Proposed Substance 120 to reduce the deleterious effects early in the development process.

In an embodiment, the Chemical Analysis Application 110 parses regulations and literature on chemicals including toxicology effects, chemical properties, chemical structures, and the like, in order to generate a Chemical Effect Graph 115 with learned weights that allow the Chemical Analysis Application 110 to associate effects with the corresponding chemical structures. Similarly, using chemical reaction literature, the Chemical Analysis Application 110 can identify reactions and include a breakdown of the chemicals involved, including the substrate, reactant, reagent, reaction, the resultant chemicals or products, and the like. This data can then be incorporated into the learned graph. In some embodiments, the Chemical Analysis Application 110 can then identify, for each component chemical of the Proposed Substance 120, the effects associated with the chemical structure, with related chemicals, and the like. The Chemical Analysis Application 110 can similarly identify reactions involving the chemical and/or similar chemicals, and continue to analyze each of the products generated by the identified reactions in a similar fashion.

In some embodiments, the Chemical Analysis Application 110 computes all potential read-across pathways in the Chemical Effect Graph 115 using a depth-first or breadth-first search, in order to calculate a minimum and/or maximum score to be compared against predefined thresholds. For example, the Chemical Analysis Application 110 may generate a score for each effect (e.g., toxicity, environmental, regulatory, and the like), and compare each against a threshold. Further, in some embodiments, the Chemical Analysis Application 110 generates an overall score based on these component scores, indicating the risk or potential for deleterious effects.

Figure 2:
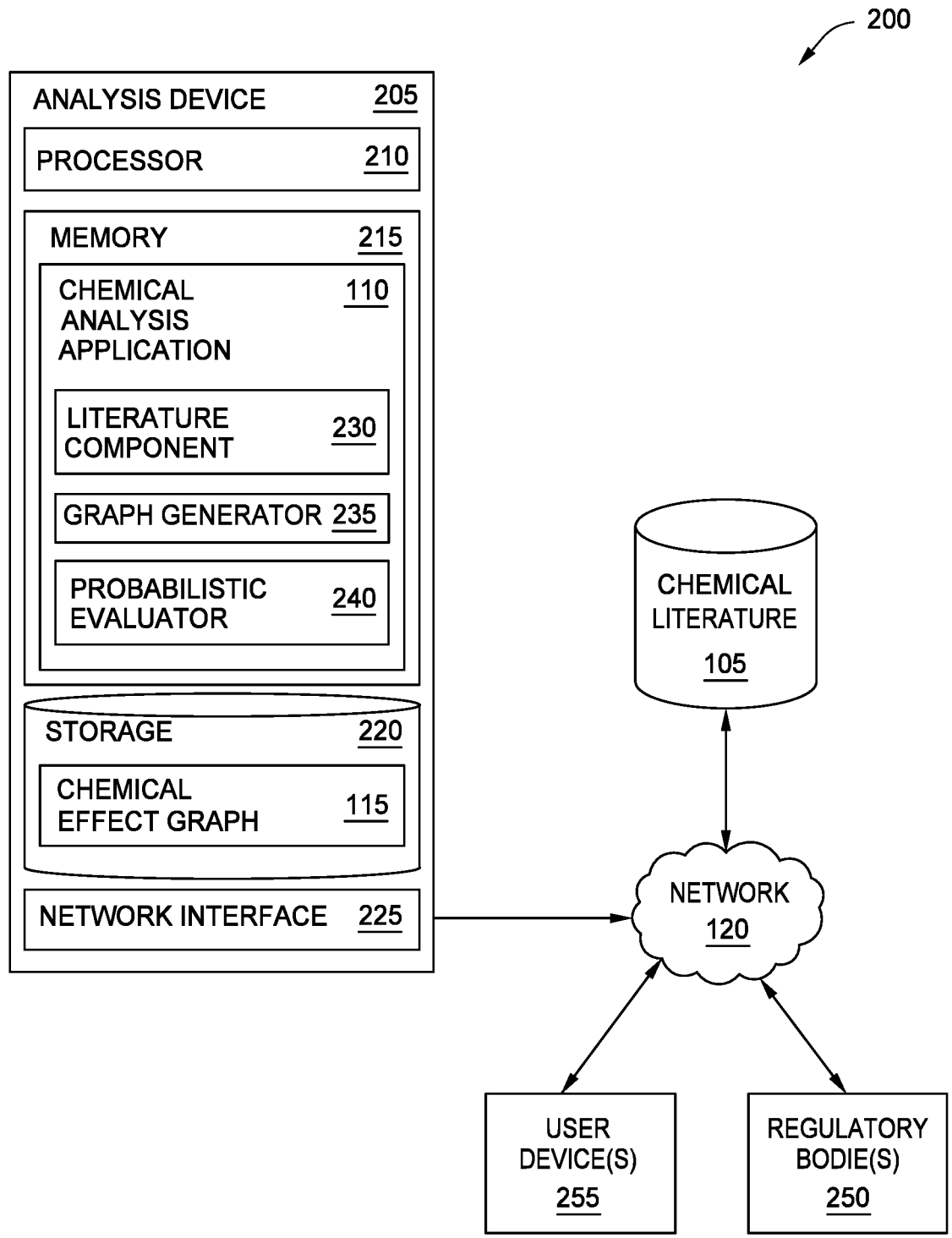
FIG. 2 is a block diagram illustrating an analysis device configured to ingest literature to automatically analyze proposed substances, according to one embodiment disclosed herein.

FIG. 2 is a block diagram illustrating an Analysis Device 205 configured to ingest literature to automatically analyze proposed substances, according to one embodiment disclosed herein. In the illustrated embodiment, the Analysis Device 205 includes a Processor 210, a Memory 215, Storage 220, and a Network Interface 225. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area network (SAN). Via the Network Interface 225, the Analysis Device 205 can be communicatively coupled with one or more other devices and storage units, including User Devices 255, data from Regulatory Bodies 250, Chemical Literature 105, and the like. In one embodiment, the Analysis Device 205 operates as part of a cloud service.

In the illustrated embodiment, the Analysis Device 205 is communicatively coupled with other devices via a Network 120. In one embodiment, the Network 120 is the Internet. Although illustrated as a physical device, in some embodiments, the Analysis Device 205 is implemented virtually (e.g., as a virtual machine, or as software executing on a server). In one embodiment, the User Devices 255 correspond to computing devices used by users to interact with the Chemical Analysis Application 110 to determine the risks involved in utilizing proposed chemical compositions. In embodiments, the User Devices 255 can correspond to desktop computers, laptop computers, mobile devices, and the like. In an embodiment, the Regulatory Bodies 250 correspond to entities that implement laws and regulations related to chemical compositions. For example, in an embodiment, the Regulatory Bodies 250 can include governmental entities at a national level, state level, local level, and the like. In one embodiment, the user can specify the relevant Regulatory Bodies 250 when analyzing new substances. In some embodiments, the user can specify a relevant location, and the Analysis Device 205 can identify the corresponding Regulatory Bodies 250.

As illustrated, the Storage 220 of the Analysis Device 205 includes a Chemical Effect Graph 115. Additionally, the Memory 215 includes a Chemical Analysis Application 110. Although illustrated as a program residing in Memory 215, in embodiments, the functionality of the Chemical Analysis Application 110 can be implemented using software, hardware, or a combination of software and hardware. In the illustrated embodiment, the Chemical Analysis Application 110 includes a Literature Component 230, a Graph Generator 235, and a Probabilistic Evaluator 240. Although depicted as discrete components for illustration, in embodiments, the operations and functionality of the Literature Component 230, Graph Generator 235, and Probabilistic Evaluator 240 may be combined or divided across any number of components.

In an embodiment, the Literature Component 230 retrieves and parses the available Chemical Literature 105 in order to understand the relevant details for each substance or composition. For example, in one embodiment, the Literature Component 230 utilizes natural language processing (NLP) to identify chemicals (or combinations of chemicals) in the Chemical Literature, and to further identify effects of the chemical(s), with respect to toxicology, environmental effects, and the like. In some embodiments, the Literature Component 230 similarly analyzes the literature to identify reactions between identified chemicals or compositions, in terms of the components (e.g., the reagent, reactant, substrate, and/or environment in which the reaction can occur) as well as the resulting product(s) (e.g., the chemicals and/or energy that is released).

In one embodiment, the Literature Component 230 also parses the Chemical Literature 105 to identify the structure of each chemical/composition. For example, the Literature Component 230 can identify the components included, determine the types and location(s) of bond(s) that make up the structure and link the components, the positioning of each component in the structure (e.g., ortho, para, or meta), and the like.

In some embodiments, the Literature Component 230 also interfaces with Regulatory Bodies 250 to identify, for each chemical or substance, any relevant regulations, laws, restrictions, and the like. For example, the Literature Component 230 may use NLP to determine whether a given chemical is banned, restricted, or otherwise subject to regulation by the relevant governmental entity (or entities). In this way, the Literature Component 230 can gather relevant details and information about individual chemicals and their reactions, in order to aid analysis of proposed new substances. In an embodiment, this information is passed to the Graph Generator 235.

In an embodiment, the Graph Generator 235 receives this parsed data and uses it to generate or update the Chemical Effect Graph 115. In one embodiment, the nodes or elements in the Chemical Effect Graph 115 each correspond to a single chemical or a combination or composition of chemicals. In some embodiments, the Graph Generator 235 includes within each node the relevant details for the chemical(s), such as the known effects, safe exposure rates, the structure of the substance, reactions involving the substance, regulations or restrictions applicable in various territories or locations, and the like. In some embodiments, the Graph Generator 235 further generates and inserts links or connections between the nodes based on similarity between them. For example, in some embodiments, for a given composition, the Graph Generator 235 generates a similarity score or measure with respect to one or more other compositions in the graph, based on the identified chemical structures.

In one embodiment, this process is iterated until a web of connections is developed that allows the Chemical Analysis Application 110 to traverse the pathways in the graph and identify related or similar compositions for a given substance. In some embodiments, the Graph Generator 235 similarly creates connections or links based on reactions between substances. For example, suppose composition A reacts with composition B to form composition C. In an embodiment, the Graph Generator 235 can generate any number of connections to reflect this reaction. In one embodiment, the Graph Generator 235 generates one or more connections that originate from the nodes representing composition A and/or composition B and terminate at the node representing composition C. In some embodiments, the connections may connect more than two nodes together. For example, connections may originate at two or more reactant nodes, merge to form a single connection representing the reaction, and/or split to lead to each resulting product. In an embodiment, the connection can include details about the reaction, such as the volume or quantity of substances involved or required, the timeline of the reaction, the environment required (e.g., if the reaction only occurs in the presence of water, oxygen, in a strong magnetic field, and the like). In other embodiments, this information is stored within each node that is relevant to the reaction.

In an embodiment, once this Chemical Effect Graph 115 is created, the Probabilistic Evaluator 240 can be used to traverse it and generate probabilistic predictions for newly proposed chemicals or compositions. For example, in one embodiment, given a proposed composition, the Probabilistic Evaluator 240 can traverse the graph to determine whether the composition has been studied in the Chemical Literature 105. If so, it will be represented in the graph. If not, in one embodiment, the Probabilistic Evaluator 240 can identify components of the composition and/or similar compositions, and iteratively traverse the graph based on these components and the learned similarity measures, in order to identify potential effects and reactions. In an embodiment, as the Probabilistic Evaluator 240 works relatively deeper through the Chemical Effect Graph 115 (e.g., to nodes that are increasingly-less relevant or similar to the proposed composition) the Probabilistic Evaluator 240 reduces the confidence in the predictions or the weight of the node, reflecting that the predicted effects indicated by the node are less likely to be accurate for the proposed substance.

In some embodiments, the Probabilistic Evaluator 240 can similarly predict the likelihood that the proposed substance will be banned or otherwise regulated, based on the data contained in the graph. In one embodiment, the Probabilistic Evaluator 240 can generate a gap measure indicating the level of uncertainty about a substance. For example, if only twenty percent of the components or structure of a proposed composition can be confidently analyzed in view of the Chemical Effect Graph 115, the Probabilistic Evaluator 240 can generate a relatively high gap measure indicating that there is significant uncertainty regarding what effect(s) the substance will have. In contrast, if nearly all of the composition can be identified, the Probabilistic Evaluator 240 can generate a relatively lower gap measure.

Figure 3:
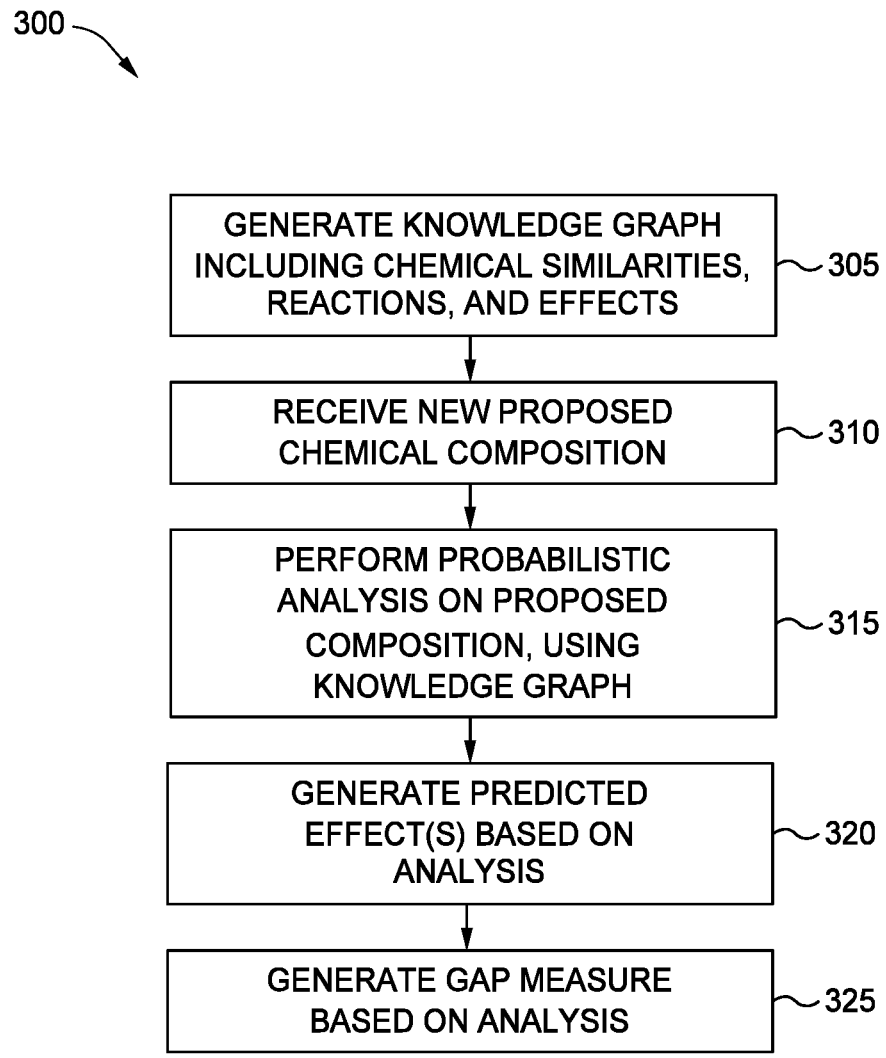
FIG. 3 is a flow diagram illustrating a method for automatically analyzing newly proposed chemical substances, according to one embodiment disclosed herein.

FIG. 3 is a flow diagram illustrating a method 300 for automatically analyzing newly proposed chemical substances, according to one embodiment disclosed herein. The method 300 begins at block 305, where a Chemical Analysis Application 110 generates a knowledge graph (e.g., a Chemical Effects Graph 115) including identified chemicals, the similarities between each substance, reactions involving each substance, and the known effects of each substance. This process is described in more detail with respect to FIG. 4, below. In the illustrated embodiment, the method 300 then proceeds to block 310, where the Chemical Analysis Application 110 receives a newly proposed chemical composition (e.g., from a user). In embodiments, this proposed substance can indicate the chemical name of the substance, the structure of the substance, and the like. At block 315, the Chemical Analysis Application 110 performs probabilistic analysis on the proposed composition using the knowledge graph. One embodiment of this analysis is described in more detail below, with respect to FIG. 5. The method 300 then continues to block 320.

At block 320, the Chemical Analysis Application 110 generates a set of predicted effects for the proposed composition, based on the probabilistic analysis. In one embodiment, this includes identifying reactions involving all or a portion of the composition (or similar chemicals), and iteratively and/or recursively identifying relevant effects and/or reactions for the products of the identified reactions. In this way, the Chemical Analysis Application 110 can generate more accurate and reliable predictions. The method 300 then proceeds to block 325, where the Chemical Analysis Application 110 generates a gap measure based on the probabilistic analysis, as described in more detail below.

Figure 4:
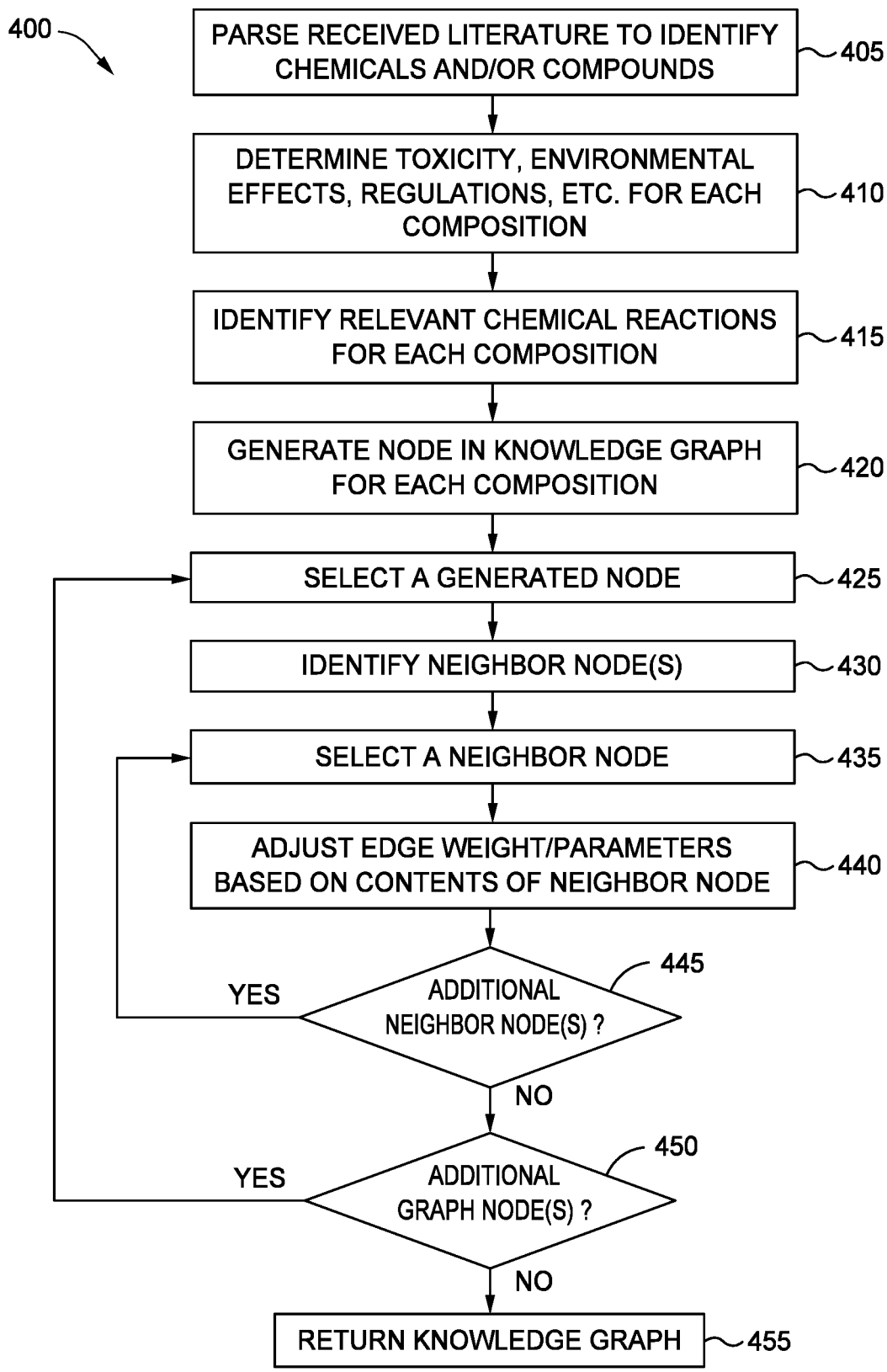
FIG. 4 is a flow diagram illustrating a method for automatically constructing a knowledge graph based on chemical literature, according to one embodiment disclosed herein.

FIG. 4 is a flow diagram illustrating a method 400 for automatically constructing a knowledge graph based on chemical literature, according to one embodiment disclosed herein. In one embodiment, the method 400 offers more detail for block 305 in FIG. 3. As illustrated, the method 400 begins at block 405, where the Chemical Analysis Application 110 parses chemical literature received from any number of sources. In one embodiment, the literature includes natural language documents pertaining to studies, experiments, and the like. In some embodiments, this parsing is completed using NLP to identify chemicals, compositions, and/or compounds that have been researched. The method 400 then proceeds to block 410, where, for each identified element, chemical, compound, or composition, the Chemical Analysis Application 110 further searches the literature to identify and extract characteristics of the composition, including toxicity, environmental effects, relevant regulations, and the like.

At block 415, the Chemical Analysis Application 110 further searches the literature to identify and extract reactions associated with each substance. In one embodiment, this includes identifying and classifying the reactants, substrate, reagents, products, and the like. The method 400 continues to block 420, where the Chemical Analysis Application 110 then generates, for each respective chemical, compound, element, or composition, a respective node in the knowledge graph. In an embodiment, each generated node includes the identified effects, regulations, and/or reactions for the corresponding chemical(s). That is, for a given composition, the corresponding node in the graph can include the toxicology, known reactions, existing regulations or restrictions, and the like. In this way, once a node is identified or selected, the Chemical Analysis Application 110 can identify the effects of the substance, as well as the reactions that may occur involving the corresponding substance. The Chemical Analysis Application 110 can then identify the node(s) associated with the products of the reaction, to analyze the potential effects of the reaction.

In some embodiments, the nodes in the knowledge graph are instantiated with no edges or connections between them. In another embodiment, all nodes are initially connected to all other nodes via a link with a default weight or value (e.g., zero), indicating no known similarity or connection. In some embodiments, edges or links are initially created and inserted based on structural similarity between each node. For example, in one embodiment, if a first composition represented by a first node shares eighty percent of its structure with a second composition represented by a second node, the Chemical Analysis Application 110 may insert a link with a relatively high weight, as compared to the edge between the first node and a third node representing a third composition that shares only five percent of its structure with the first composition. In this way, the initial edge weights between any given nodes indicate the level of structural similarity between the corresponding compounds or chemicals. Although this structural similarity can be an important initial clue, for many chemicals, relatively minor structural differences can yield radically different reactions and toxicology. The method 400 then proceeds to block 425.

At block 425, the Chemical Analysis Application 110 selects one of the generated nodes. The method then continues to block 430, where the Chemical Analysis Application 110 identifies any neighboring nodes. In one embodiment, identifying neighboring nodes includes identifying any other nodes in the graph that have a connection, edge, or link to the selected node (or have an edge with a predefined minimum weight). In another embodiment, if no edges or links have been created, the Chemical Analysis Application 110 identifies nodes representing chemical compositions that share at least a portion of the structure of the composition represented by the selected node. In another embodiment, the Chemical Analysis Application 110 selects all nodes in the graph at this stage. Once the relevant nodes have been identified, the method 400 proceeds to block 435, where one of the identified nodes is selected.

At block 440, the Chemical Analysis Application 110 determines the characteristics of the selected neighbor node, and creates or modifies the parameters of the edge connecting the two nodes based on these characteristics. In one embodiment, this includes adjusting the weight of the edge based on the structural similarity of the two compositions. For example, in one such embodiment, the Chemical Analysis Application 110 sets the weight of the edge based in part on a percentage of the chemical structures that are shared between the compositions represented by each node, such that more similar structures yield higher weights. Similarly, in some embodiments, the weight is adjusted based in part on whether the two compositions are treated similarly (or identically) by regulatory bodies. For example, if a single regulation (or a single section or portion of the regulation) applies to both of the compositions, the Chemical Analysis Application 110 can increase the weight of the connection, as compared to compositions that are treated differently by the law.

In some embodiments, the Chemical Analysis Application 110 further defines the edge weight or strength based on the effects caused by the substances associated with each node. In such an embodiment, the edge between two nodes will be given a higher weight if the corresponding chemical compositions or compounds have similar effects, as compared to compounds with dissimilar effects. For example, if both chemicals have the same or similar toxicology results, the Chemical Analysis Application 110 will assign a relatively high weight to the edge. In contrast, if one is known to be carcinogenic and the other is known to be non-carcinogenic, the corresponding edge will be given a relatively low weight, with respect to toxicology.

In some embodiments, a separate edge weight is generated for each type of relationship. That is, there may be a weight representing the structural similarity, a weight representing the regulatory similarity, a weight representing the toxicological similarity, a weight representing the environmental similarity, and the like. In such an embodiment, the graph generated by the Chemical Analysis Application 110 includes detail regarding how similar two given nodes are, across each available domain, based on the available literature. Thus, two compositions can have edges indicating they are very structurally similar but dissimilar with respect to toxicology, are closely aligned in their environmental effects but are structurally dissimilar, and the like. The method 400 then proceeds to block 445.

At block 445, the Chemical Analysis Application 110 determines whether there is at least one additional neighbor node that has not yet been processed for the selected node. In one embodiment, this includes determining whether there is at least one other node that either does not have any edges generated to the selected node, or whether there are any nodes with edges using a "default" or unrefined value. If so, the method 400 returns to block 435. Otherwise, the method 400 continues to block 450. At block 450, the Chemical Analysis Application 110 determines whether there are any nodes remaining in the knowledge graph that have not yet been analyzed to generate appropriate edge weights. If so, the method 400 returns to block 425. Otherwise, the method 400 continues to block 455.

At block 455, the Chemical Analysis Application 110 stores and/or returns the knowledge graph for future use. In some embodiments, the Chemical Analysis Application 110 can repeat all or a portion of the method 400 for any newly identified literature. For example, in one embodiment, whenever a new document (e.g., a new study, regulation, experiment, and the like) becomes available, the Chemical Analysis Application 110 can analyze it using NLP to ingest its information into the graph. That is, the Chemical Analysis Application 110 can generate new nodes as needed (e.g., if the document relates to a substance that is not yet reflected in the graph), revise existing nodes (e.g., if the document indicates newly discovered effects, reactions, or regulations affecting an existing chemical), and/or revise connections between nodes (e.g., if the document discusses newly found similarities, relationships, effects, etc.), and the like. In this way, the Chemical Analysis Application 110 can learn appropriate weights to use for probabilistic analysis and predictions. In some embodiments, using the generated graph, the Chemical Analysis Application 110 can similarly identify which effect(s) tend to be associated with various chemical structure(s). In some embodiments, while in use, the Chemical Analysis Application 110 can further refine the graph based on user input, as discussed below in more detail.

Figure 5:
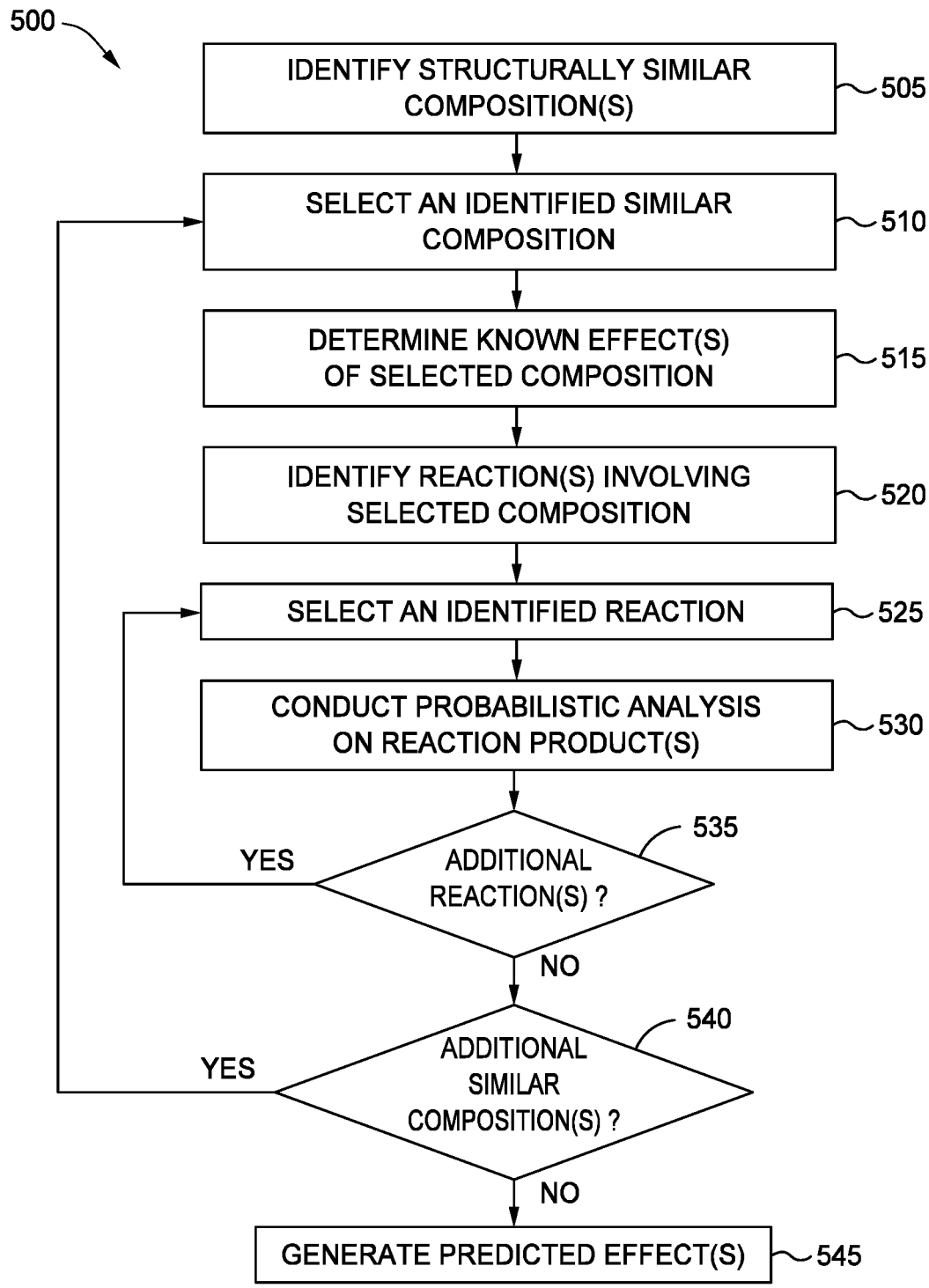
FIG. 5 is a flow diagram illustrating a method for using probabilistic analysis to evaluate a proposed substance in view of similar substances found in existing literature, according to one embodiment disclosed herein.

FIG. 5 is a flow diagram illustrating a method 500 for using probabilistic analysis to evaluate a proposed substance in view of similar substances found in existing literature, according to one embodiment disclosed herein. The method 500 begins when the Chemical Analysis Application 110 receives an indication of a newly proposed chemical substance, composition, and/or compound for analysis. For example, if a user plans to use the new substance in a product, they may wish to analyze it in view of the knowledge graph in order to ensure it will not have unexpected effects. At block 505, the Chemical Analysis Application 110 identifies any structurally similar compositions in the knowledge graph. In one embodiment, if the proposed composition itself exists in the graph, the Chemical Analysis Application 110 includes the corresponding node in the list of structurally-similar substances.

In some embodiments, the Chemical Analysis Application 110 uses a predefined threshold to identify structurally similar compounds. For example, in one embodiment, the Chemical Analysis Application 110 can identify the substances that share at least fifty percent of the structure of the indicated new compound. In an embodiment, the Chemical Analysis Application 110 can analyze the connections in the knowledge graph to identify similar compounds. For example, the Chemical Analysis Application 110 can traverse the graph to identify a set of compositions that are within a predefined structural similarity to the proposed compound. In some embodiments, the Chemical Analysis Application 110 can then iteratively traverse the graph for each respective identified similar compound, to identify further compositions that are sufficiently similar to the respective composition. In one embodiment, while traversing the graph, the Chemical Analysis Application 110 can identify compositions that are similar with respect to effects, regulations, and the like (e.g., in addition to or instead of looking only for structural similarity). In an embodiment, this process can repeat until a predefined number of compositions are found, until the predefined threshold of similarity is not met, and the like.

As illustrated, the method 500 then proceeds to block 510, where the Chemical Analysis Application 110 selects one of the identified similar compositions. At block 515, the Chemical Analysis Application 110 analyzes the corresponding node in the knowledge graph to determine the effects and/or regulations that are associated with the selected substance. For example, in an embodiment, the Chemical Analysis Application 110 can determine whether the selected substance is regulated or banned, whether it has any known toxicological effects, whether it is linked to negative environmental effects, and the like. In one embodiment, this information is retained for each similar composition, so that the Chemical Analysis Application 110 can generate overall predictions for the proposed composition, as discussed in more detail below. The method 500 then continues to block 520, where the Chemical Analysis Application 110 identifies any reactions that include the selected composition as a reactant, reagent, substrate, and the like. That is, in the illustrated embodiment, the Chemical Analysis Application 110 identifies any reactions for which the selected composition acts as an input or medium in which the reaction occurs, as opposed to a product of the reaction.

The method 500 then continues to block 525, where the Chemical Analysis Application 110 selects one of the identified reactions. At block 530, the Chemical Analysis Application 110 identifies the product(s) generated by the selected reaction, and conducts a probabilistic analysis on each of these products. In one embodiment, the Chemical Analysis Application 110 performs this probabilistic analysis by recursively completing the method 500 for each identified product. That is, in one embodiment, the Chemical Analysis Application 110 can, for each product, identify the effects of the product, identify similar compositions for the same iterative analysis, and identify reactions involving the product. In embodiments, the products produced by these secondary reactions can also be similarly analyzed. In this way, the Chemical Analysis Application 110 can traverse across all (relevant) pathways in the knowledge graph to analyze the probabilities and risks involved at each step. In embodiments, this traversal can be completed depth-first or breadth-first, depending on the particular implementation.

In some embodiments, conducting the probabilistic analysis on the reaction products includes determining a likelihood that the reaction will occur at all. For example, in one such embodiment, the Chemical Analysis Application 110 can determine how common the other required reactant(s) are, in order to determine how likely the reaction is to take place. In some embodiments, the user can specify an intended use or environment, and the Chemical Analysis Application 110 can determine whether the other required reactant(s) are likely to be found in such a use. For example, if the selected reaction can only occur in pure nitrogen environments, the Chemical Analysis Application 110 may determine that the reaction is unlikely to occur if the proposed chemical is to be used in a household furniture cleaner. Similarly, if the reaction requires significant energy input, or can only occur using a specific mechanism or device, the Chemical Analysis Application 110 can determine a likelihood that these circumstances will occur, based on the indicated use. In some embodiments, if there is uncertainty, the Chemical Analysis Application 110 can prompt the user to indicate whether the required reactant(s) and/or circumstances are likely to be present.

At block 535, the Chemical Analysis Application 110 determines whether there is at least one additional reaction that is yet to be analyzed, with respect to the selected similar composition. If so, the method 500 iterates through each such reaction. If not, the method 500 proceeds to block 540, where the Chemical Analysis Application 110 determines whether there are any remaining similar compositions to be so analyzed. If so, the method 500 returns to block 510 to select the next one. Otherwise, the method 500 continues to block 545, where the Chemical Analysis Application 110 generates the predicted effect(s) for the newly proposed chemical, composition, substance, or compound.

In one embodiment, the Chemical Analysis Application 110 generates these predicted effects by aggregating the information gathered during the above-discussed graph traversal. In one embodiment, this includes generating a toxicology risk score, an environmental risk score, and/or a regulatory risk score for each composition or element included in the analysis. For example, when effect information is collected for a given composition at block 515, the Chemical Analysis Application 110 may generate one or more scores for the particular node, and retain this data to aid the final computation. In one embodiment, the Chemical Analysis Application 110 generates separate measures or scores for each domain. In such an embodiment, the Chemical Analysis Application 110 can generate predicted toxicology, a predicted regulatory result, a predicted environmental effect, and the like.

In some embodiments, when aggregating the data collected with respect to each respective composition, the Chemical Analysis Application 110 determines the similarity between the respective composition and the received new composition. For example, if the respective composition is highly similar to the proposed composition (e.g., structurally), the Chemical Analysis Application 110 can assign a relatively higher weight to the effects of the respective composition. In this way, compositions that are likely to be similar have more influence on the final predictions, because their respective effects are given higher weights. Similarly, in some embodiments, the Chemical Analysis Application 110 includes consideration as to how likely a given reaction is to occur, when determining how much weight to give the corresponding effect(s).

In one embodiment, the predicted effect(s) include a quantitative likelihood for each specific risk. For example, in such an embodiment, the Chemical Analysis Application 110 can generate likelihoods that the substance will cause carcinogenic effects, respiratory concerns, irritation, and the like. In some embodiments, these categories can be as specific or general as desired, depending on the particular implementation and/or the input provided by the user. In one embodiment, if the generated probability of a given result is below a predefined threshold, the Chemical Analysis Application 110 can ignore this result. In some embodiments, the generated prediction(s) include a quantitative measure of the likelihood of each particular domain being problematic. For example, based on the potential effects (e.g., that the substance will be, or will be involved in a reaction that produces, a carcinogenic substance), as well as the potential likelihood of each effect, the Chemical Analysis Application 110 can generate an overall toxicology risk. In an embodiment, this domain probably can be a number (e.g., between zero and ten) indicating the likelihood that the proposed new substance will be problematic or dangerous with respect to the given domain. This process can be repeated for each domain (e.g., for environmental risks, for toxicological risk, for regulatory risks, and the like). In an embodiment, if the generated score in a given domain exceeds a threshold, the Chemical Analysis Application 110 generate an alert to indicate that the proposed substance is risky, dangerous, or that the user should proceed with caution.

In some embodiments, based on this probabilistic analysis, the Chemical Analysis Application 110 can further generate a gap measure indicating the risk or uncertainty surrounding the proposed substance. In one embodiment, the Chemical Analysis Application 110 generates this score based on the percentage or portion of the proposed substance that could be adequately analyzed, in view of the knowledge graph. In one embodiment, to generate the gap measure, the Chemical Analysis Application 110 determines which of the identified similar compositions is most structurally-similar to the proposed composition. In some embodiments, the Chemical Analysis Application 110 generates similarity measures (e.g., indicating the percentage of the respective chemical structures that are shared). The highest such similarity measure (or its inverse) can then be used as the gap measure. In some embodiments, if the gap measure exceeds a predefined threshold the Chemical Analysis Application 110 flags the proposed substance as risky, uncertain, or otherwise unclear.

In some embodiments, in addition to determining the percentage of the shared chemical structure, the Chemical Analysis Application 110 can also determine how important the unshared structure is. For example, suppose ninety percent of the proposed chemical substance can be found and analyzed. In some embodiments, this would lead to a relatively low gap measure. However, suppose that the Chemical Analysis Application 110 determines based on the knowledge graph that the remaining ten percent tends to be highly relevant in determining the particular effects. In such an embodiment, the Chemical Analysis Application 110 can increase the gap measure, based on determining that the unknown structure may have a significant impact on the effects of the chemical. In embodiments of the present disclosure, the Chemical Analysis Application 110 can generate and return objective and quantitative measures of the potential risks involved in producing or using a given chemical substance. In addition to being quicker, these predictions are more accurate, less subjective, and more thorough than those provided using existing approaches.

Figure 6:
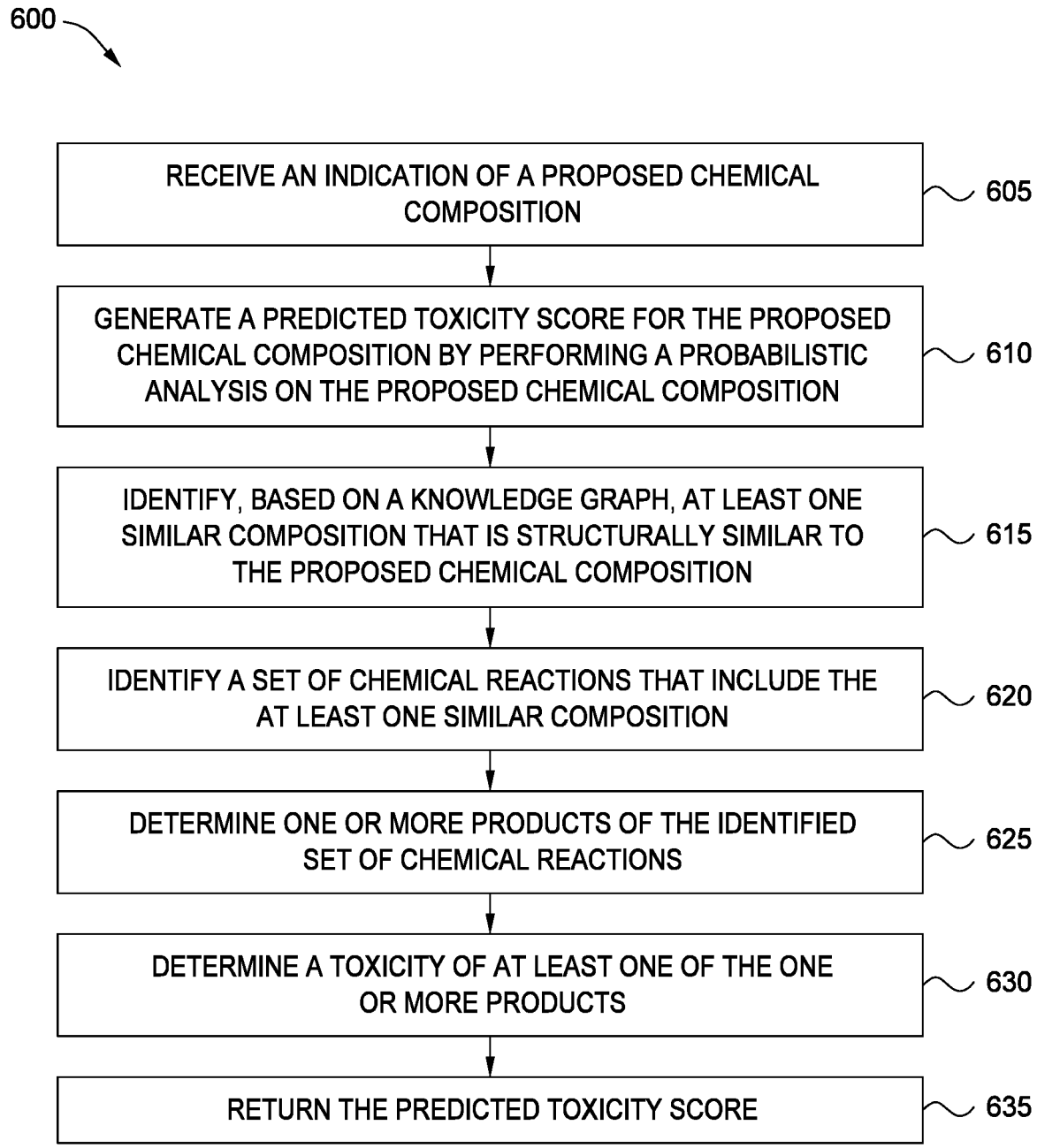
FIG. 6 is a flow diagram illustrating a method for automatically analyzing proposed substances using a knowledge graph, according to one embodiment disclosed herein.

FIG. 6 is a flow diagram illustrating a method 600 for automatically analyzing proposed substances using a knowledge graph, according to one embodiment disclosed herein. The method 600 begins at block 605, where a Chemical Analysis Application 110 receives an indication of a proposed chemical composition. The method 600 then proceeds to block 610, where the Chemical Analysis Application 110 generates a predicted toxicity score for the proposed chemical composition by performing a probabilistic analysis on the proposed chemical composition. In an embodiment, this probabilistic analysis includes performing blocks 615 through 630. At block 615, the Chemical Analysis Application 110 identifies, based on a knowledge graph, at least one similar composition that is structurally similar to the proposed chemical composition. The method 600 then continues to block 620, where the Chemical Analysis Application 110 identifies a set of chemical reactions that include the at least one similar composition. Additionally, at block 625, the Chemical Analysis Application 110 determines one or more products of the identified set of chemical reactions. Further, at block 630, the Chemical Analysis Application 110 determines a toxicity of at least one of the one or more products.

Finally, the method 600 proceeds to block 635, where the Chemical Analysis Application 110 returns the predicted toxicity score.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Chemical Analysis Application 110) or related data available in the cloud. For example, the Chemical Analysis Application 110 could execute on a computing system in the cloud and analyze proposed chemicals using the knowledge graph. In such a case, the Chemical Analysis Application 110 could probabilistically analyze risks involved in new substances, and store the knowledge graph at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   receiving a first indication of a first proposed chemical composition;
   generating a first predicted toxicity score for the first proposed chemical composition by performing, by operation of one or more computer processors, a probabilistic read-across analysis on the first proposed chemical composition, wherein performing the probabilistic read-across analysis comprises:
   identifying, based on a knowledge graph, at least one similar composition that is structurally similar to the first proposed chemical composition, wherein the knowledge graph comprises:
      a plurality of nodes, each respective node corresponding to a respective chemical composition, and
      a plurality of edges indicating learned structural similarity among chemical compositions, wherein at least one of the plurality of edges comprises a strength defined based on regulatory similarity, with respect to at least one regulatory body, between corresponding chemical compositions;
   identifying a set of chemical reactions that include the at least one similar composition;
   determining one or more products of the identified set of chemical reactions; and
   determining a toxicity of at least one of the one or more products; and
   returning the first predicted toxicity score;
   receiving a second indication of a second proposed chemical composition, wherein the second proposed chemical composition comprises a modification to the first proposed chemical composition selected based on the first predicted toxicity score; and
   generating a second predicted toxicity score for the second proposed chemical composition, wherein the second predicted toxicity score provides an understanding regarding potential risks of the second proposed chemical composition and can be used to ensure that the second proposed chemical composition will not be potentially dangerous or toxic.

2. The method of claim 1, the method further comprising:
   receiving information about a plurality of chemical compositions, the information including environmental and toxicological effects of each of the plurality of chemical compositions;
   receiving information about a plurality of chemical reactions possible among the plurality of chemical compositions; and
   generating the knowledge graph reflecting the plurality of chemical compositions and the plurality of chemical reactions.

3. The method of claim 2, the method further comprising generating one or more connections in the knowledge graph based on similarity between each of the plurality of chemical compositions, wherein the similarity includes:
   (i) a structural similarity;
   (ii) a toxicological similarity;
   (iii) an environmental similarity; and
   (iv) a regulatory similarity.

4. The method of claim 1, wherein performing the probabilistic read-across analysis on the proposed chemical composition comprises recursively traversing the knowledge graph by:
   identifying a respective plurality of similar compositions that are structurally similar to the proposed chemical composition;
   identifying, for each respective similar composition of the respective plurality of similar compositions, a respective set of chemical reactions;
   determining one or more products of each respective chemical reaction in the respective set of chemical reactions; and
   determining respective toxicities of each of the one or more products.

5. The method of claim 1, the method further comprising:
   generating a gap measure based on the probabilistic read-across analysis; and
   upon determining that the gap measure exceeds a predefined threshold, generating an alert indicating that using the proposed chemical composition is uncertain.

6. The method of claim 1, the method further comprising:
   generating, based on the probabilistic read-across analysis, a predicted likelihood that the proposed chemical composition will be regulated by a relevant government entity.

7. The method of claim 1, the method further comprising:
   generating a confidence value for the predicted toxicity score, based on the probabilistic read-across analysis; and
   upon determining that the confidence value is above a predefined threshold, generating an alert indicating that using the proposed chemical composition is dangerous.

8. A computer-readable storage medium having computer-readable program code embodied therewith, the computer-readable program code executable by one or more computer processors to perform an operation comprising:
   receiving an indication of a proposed chemical composition;
   generating a predicted toxicity score for the proposed chemical composition by performing, by operation of one or more computer processors, a probabilistic read-across analysis on the proposed chemical composition, wherein performing the probabilistic read-across analysis comprises:
   identifying, based on a knowledge graph, at least one similar composition that is structurally similar to the proposed chemical composition, wherein the knowledge graph comprises:
      a plurality of nodes, each respective node corresponding to a respective chemical composition, and
      a plurality of edges indicating learned structural similarity among chemical compositions, wherein at least one of the plurality of edges comprises a strength defined based on regulatory similarity, with respect to at least one regulatory body, between corresponding chemical compositions;
   identifying a set of chemical reactions that include the at least one similar composition;
   determining one or more products of the identified set of chemical reactions; and
   determining a toxicity of at least one of the one or more products; and
   returning the predicted toxicity score, wherein the predicted toxicity score provides an understanding regarding potential risks of the proposed chemical composition and can be used to ensure that the proposed chemical composition will not be potentially dangerous or toxic.

9. The computer-readable storage medium of claim 8, the operation further comprising:
receiving information about a plurality of chemical compositions, the information including environmental and toxicological effects of each of the plurality of chemical compositions;
receiving information about a plurality of chemical reactions possible among the plurality of chemical compositions; and
generating the knowledge graph reflecting the plurality of chemical compositions and the plurality of chemical reactions.

10. The computer-readable storage medium of claim 9, the operation further comprising generating one or more connections in the knowledge graph based on similarity between each of the plurality of chemical compositions, wherein the similarity includes:
(i) a structural similarity;
(ii) a toxicological similarity;
(iii) an environmental similarity; and
(iv) a regulatory similarity.

11. The computer-readable storage medium of claim 8, wherein performing the probabilistic read-across analysis on the proposed chemical composition comprises recursively traversing the knowledge graph by:
identifying a respective plurality of similar compositions that are structurally similar to the proposed chemical composition;
identifying, for each respective similar composition of the respective plurality of similar compositions, a respective set of chemical reactions;
determining one or more products of each respective chemical reaction in the respective set of chemical reactions; and
determining respective toxicities of each of the one or more products.

12. The computer-readable storage medium of claim 8, the operation further comprising:
generating a gap measure based on the probabilistic read-across analysis; and
upon determining that the gap measure exceeds a predefined threshold, generating an alert indicating that using the proposed chemical composition is uncertain.

13. The computer-readable storage medium of claim 8, the operation further comprising:
generating, based on the probabilistic read-across analysis, a predicted likelihood that the proposed chemical composition will be regulated by a relevant government entity.

14. The computer-readable storage medium of claim 8, the operation further comprising:
generating a confidence value for the predicted toxicity score, based on the probabilistic read-across analysis; and
upon determining that the confidence value is above a predefined threshold, generating an alert indicating that using the proposed chemical composition is dangerous.

15. A system comprising:
one or more computer processors; and
a memory containing a program which when executed by the one or more computer processors performs an operation, the operation comprising:
receiving an indication of a proposed chemical composition;
generating a predicted toxicity score for the proposed chemical composition by performing a probabilistic read-across analysis on the proposed chemical composition, wherein performing the probabilistic read-across analysis comprises:
identifying, based on a knowledge graph, at least one similar composition that is structurally similar to the proposed chemical composition, wherein the knowledge graph comprises:
a plurality of nodes, each respective node corresponding to a respective chemical composition, and
a plurality of edges indicating learned structural similarity among chemical compositions, wherein at least one of the plurality of edges comprises a strength defined based on regulatory similarity, with respect to at least one regulatory body, between corresponding chemical compositions;
identifying a set of chemical reactions that include the at least one similar composition;
determining one or more products of the identified set of chemical reactions; and
determining a toxicity of at least one of the one or more products; and
returning the predicted toxicity score, wherein the predicted toxicity score provides an understanding regarding potential risks of the proposed chemical composition and can be used to ensure that the proposed chemical composition will not be potentially dangerous or toxic.

16. The system of claim 15, the operation further comprising:
receiving information about a plurality of chemical compositions, the information including environmental and toxicological effects of each of the plurality of chemical compositions;
receiving information about a plurality of chemical reactions possible among the plurality of chemical compositions;
generating the knowledge graph reflecting the plurality of chemical compositions and the plurality of chemical reactions; and
generating one or more connections in the knowledge graph based on similarity between each of the plurality of chemical compositions, wherein the similarity includes:
(i) a structural similarity;
(ii) a toxicological similarity;
(iii) an environmental similarity; and
(iv) a regulatory similarity.

17. The system of claim 15, wherein performing the probabilistic read-across analysis on the proposed chemical composition comprises recursively traversing the knowledge graph by:
identifying a respective plurality of similar compositions that are structurally similar to the proposed chemical composition;
identifying, for each respective similar composition of the respective plurality of similar compositions, a respective set of chemical reactions;
determining one or more products of each respective chemical reaction in the respective set of chemical reactions; and
determining respective toxicities of each of the one or more products.

18. The system of claim 15, the operation further comprising:
   generating a gap measure based on the probabilistic read-across analysis; and
   upon determining that the gap measure exceeds a predefined threshold, generating an alert indicating that using the proposed chemical composition is uncertain.

19. The system of claim 15, the operation further comprising:
   generating, based on the probabilistic read-across analysis, a predicted likelihood that the proposed chemical composition will be regulated by a relevant government entity.

20. The system of claim 15, the operation further comprising:
   generating a confidence value for the predicted toxicity score, based on the probabilistic read-across analysis; and
   upon determining that the confidence value is above a predefined threshold, generating an alert indicating that using the proposed chemical composition is dangerous.

* * * * *